United States Patent [19]

Harwich

[11] Patent Number: 5,203,281
[45] Date of Patent: Apr. 20, 1993

[54] COLLAPSIBLE FEEDER AND PROTECTIVE ENCLOSURE

[76] Inventor: Mary B. Harwich, P.O Box 533, Glencoe, Ill. 60022

[21] Appl. No.: 879,025

[22] Filed: May 6, 1992

[51] Int. Cl.⁵ .............................................. A01K 5/00
[52] U.S. Cl. ..................................................... 119/57.9
[58] Field of Search ................. 119/57.9, 57.8, 52.3, 119/52.4, 51.5, 23, 26

[56] References Cited

U.S. PATENT DOCUMENTS

| | | | |
|---|---|---|---|
| 865,173 | 9/1907 | Eichberg | 119/23 X |
| 2,799,244 | 7/1957 | Dorsey | |
| 2,845,895 | 8/1958 | Balkauskas | |
| 3,399,650 | 9/1968 | Goodman | 119/57.9 X |
| 4,434,745 | 3/1984 | Perkins et al. | 119/57.9 |
| 4,441,272 | 4/1984 | Bartz | 119/23 X |
| 4,524,721 | 6/1985 | Lanner et al. | |
| 4,648,351 | 3/1987 | Lanner et al. | |
| 4,821,451 | 4/1989 | Matson | 43/105 X |
| 4,864,770 | 9/1989 | Serio | 43/105 |
| 5,016,573 | 5/1991 | Power | 119/57.8 X |
| 5,111,772 | 5/1992 | Lipton | 119/57.9 |

Primary Examiner—Gene Mancene
Assistant Examiner—Thomas Price
Attorney, Agent, or Firm—Lockwood, Alex, Fitzgibbon & Cummings

[57] ABSTRACT

An improved collapsible protective enclosure for feeding butterflies and the like includes a cylindrical sidewall having circumferential ribs and therebetween a mesh material having members sufficiently spaced from each other to allow the ingress and egress of butterflies and the like while excluding larger animals. The sidewall further includes a peripheral flange at each end of the protective enclosure to provide opened or closed ends. A feeding platform and ant guard assembly can also be included, and the protective enclosure may hang in either a vertical or a horizontal orientation.

22 Claims, 3 Drawing Sheets

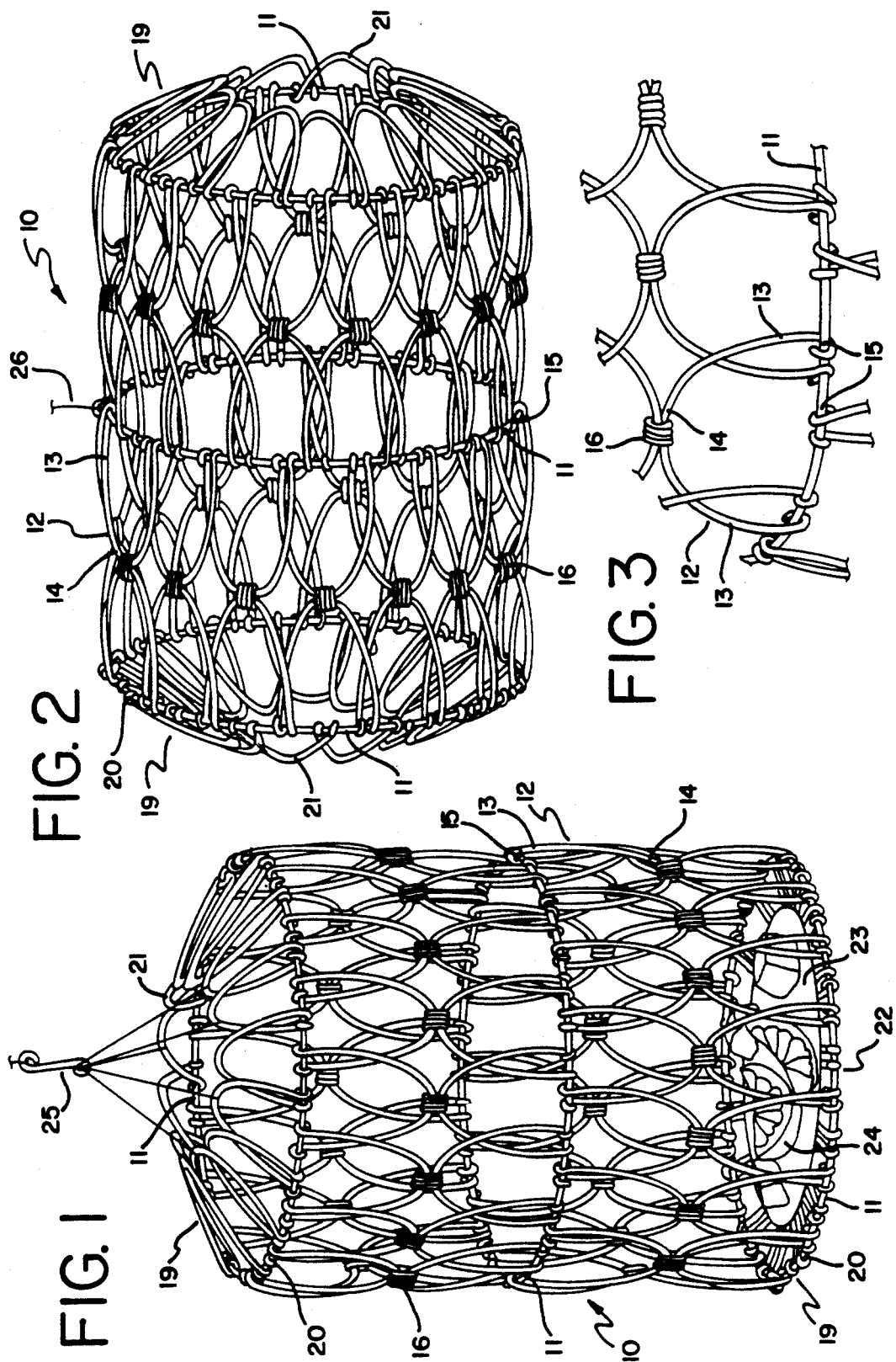

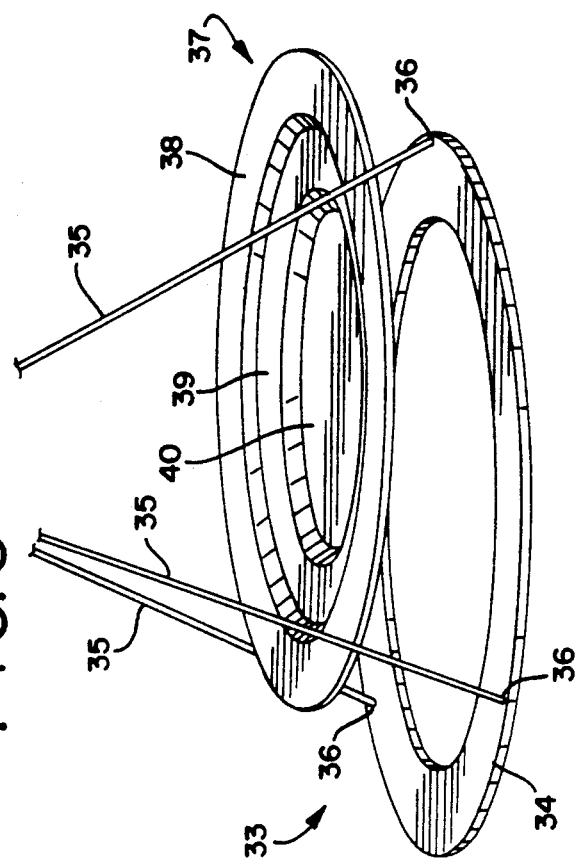
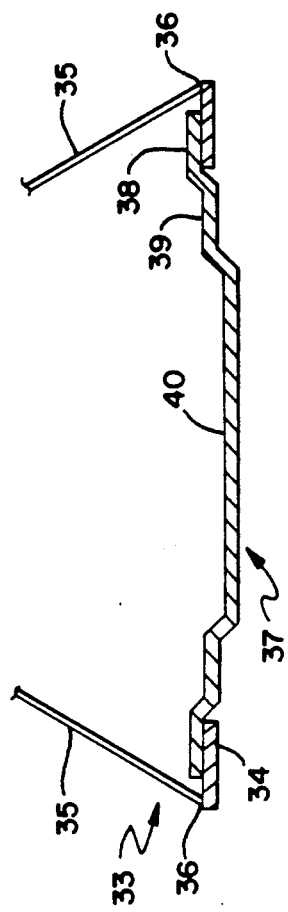
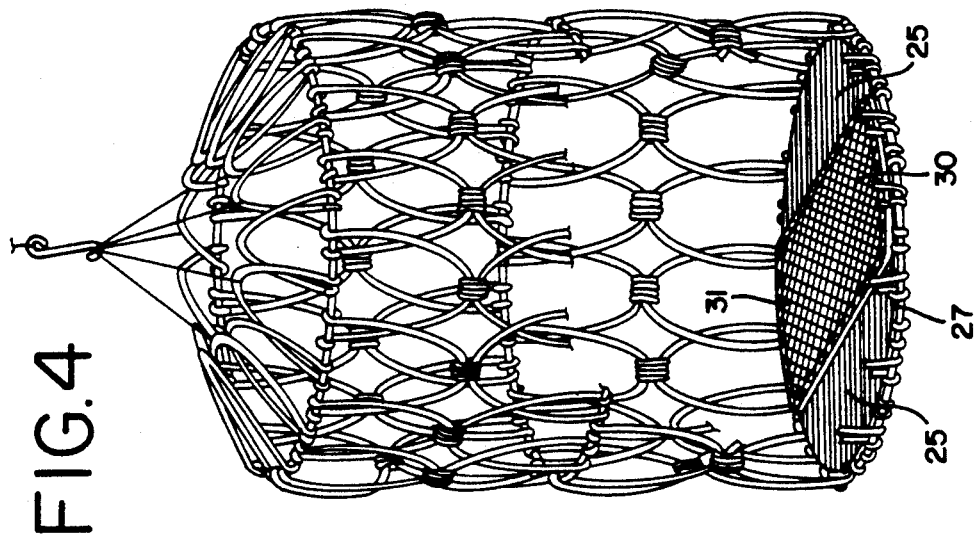

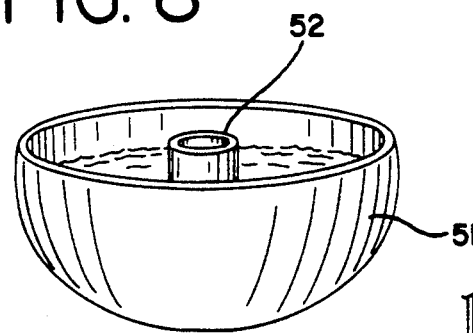
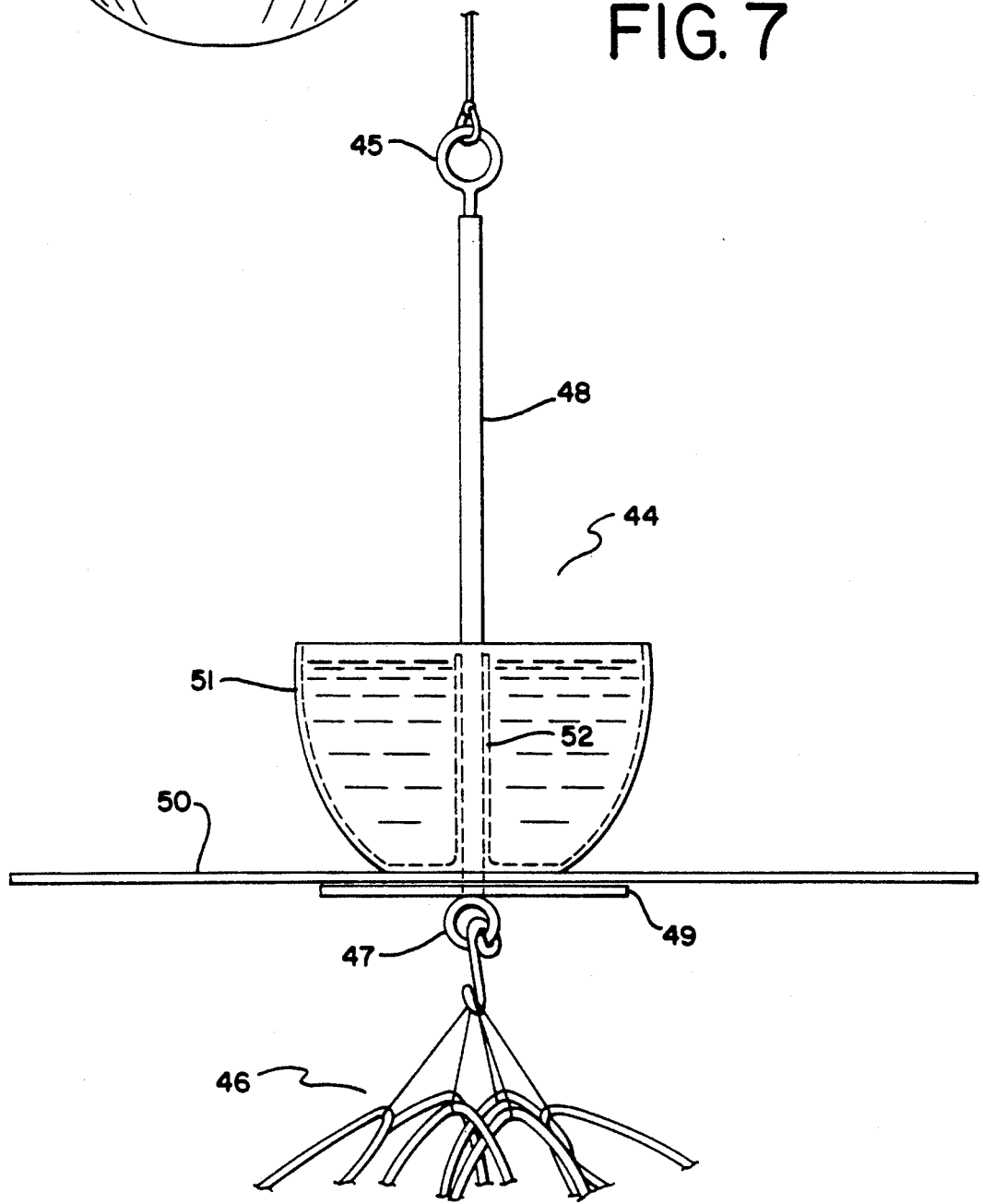

COLLAPSIBLE FEEDER AND PROTECTIVE ENCLOSURE

BACKGROUND OF THE INVENTION

The present invention relates to a collapsible protective enclosure for feeding butterflies and the like. More particularly, the invention relates to a new and improved collapsible enclosure for feeding butterflies and the like while protecting them from larger animals such as birds by preventing or discouraging such larger animals from entering the feeder.

A variety of collapsible cages are commonly known in the art. In U.S. Pat. No. 2,799,244 a collapsible bird cage is described having a rigid central rod member encircled by a plurality of tensioned limp flexible members; such as threads, strings or cords. The resulting overall design has sidewalls which are flimsy and cannot support appendages for a cage nor the weight of even a small animal in a stable manner. This design also has a disadvantage that both ends of the cage must remain closed to the outside.

In U.S. Pat. No. 2,845,895 a collapsible cage is described which has a frustro-conical sidewall attached to a flat circular top and a circular pan-shaped bottom secured by rounded lugs or clips. This design also has a disadvantage in that it does not allow for an orientation in which both the top and the bottom may remain open. Nor do these examples of collapsible cages include or allow for specially designed feeding trays.

In order to overcome the deficiencies of the prior art, it is an object of the present invention to provide an improved collapsible protective enclosure and feeder which is constructed in a manner to allow the ingress and egress of butterflies and the like while simultaneously substantially impeding the ingress of larger animals which may consume the food and/or harm or destroy the butterflies and the like.

It is another object of the present invention to provide an improved collapsible protective enclosure and feeder which may be suspended in either a horizontal or a vertical orientation.

It is a further object of the invention to provide an improved collapsible generally enclosed feeder which allows for the suspension of a feeding platform.

It is a still another object of the invention to provide an improved generally enclosed feeder for butterflies and the like which may be vertically collapsed into a small easily movable shape.

It is a further object of the invention to provide an improved collapsible feeding device made of a low cost, attractive, rugged material which provides for prolonged use of the feeding device outdoors.

It is still another object of the invention to provide an improved collapsible feeding device having an ant guard and rain shield suspended above the feeder.

SUMMARY OF THE INVENTION

In accordance with these and other objects, the present invention provides an improved collapsible protective enclosure for feeding butterflies and the like. The feeder comprises a generally cylindrical sidewall including at least two circumferential ribs located at the peripheral ends of said sidewall. The sidewall is made of multiple U-shape members assembled to form a mesh material having a spacing between said U-shaped members sufficient to have the mesh material allow ingress and egress of butterflies and the like while excluding larger animals. The U-shaped members each have an apex portion and a leg portion. The leg portions are pivotally mounted to the circumferential ribs. Between the circumferential ribs, the U-shaped members are in opposition to each other at their respective apexes. These apexes are joined via attachment means between the U-shaped members. The attachment means are spaced concentrically at a uniform distance from the circumferential ribs and form opposing segments each composed of a plurality of U-shaped members, each said segment being rotatable on one of said ribs to impart a collapsibility characteristic to the feeder.

The sidewall further preferably includes at least one end having a peripheral flange comprising multiple U-shaped members pivotally attached at the leg portions to the circumferential rib. The U-shaped members are unattached at the apex portions to enable the peripheral flange to be movable inwardly to close the end of the feeder, or outwardly to open the end of the feeder.

The collapsible generally enclosed feeder may also include a feeding platform comprising a circular rim including a multi-level plate insertible into the rim. The uppermost level of the plate may be placed in parallel contact with the rim. This feeding platform includes means for supporting it within the feeder.

An advantageous feature of the invention is that the feeder further includes means for hanging in either a vertical or a horizontal orientation. These alternate orientations allow the feeder to be more easily customized to varying surroundings and conditions.

In accordance with this invention, when the feeder is in a horizontal position or orientation, the peripheral flanges at the sides of the feeder may be in an open position. Butterflies and the like are able to fly in the open ends and through the feeder as well as through the mesh sides. In this horizontal orientation, the feeding platform may also be suspended inside the device in order to allow for a place to put fruits and other food that will attract butterflies. Even when the generally enclosed feeder is in this horizontal position, butterflies inside the feeder will be protected from swooping birds and other animals. Due to the opened position of the peripheral flanges, birds are substantially prevented from entering directly into the generally open end of the feeder without first landing on the outer extremities of the sidewalls. Such a landing by a bird on the sidewalls of the feeder will alert the butterflies to the presence of a predator and the butterflies to easily escape.

In accordance with this invention, hanging the feeder in a vertical position or orientation will allow the bottom peripheral flange, when provided, to be moved to a generally closed position in order to support a feeding plate for placing fruit or other foods which will attract butterflies and the like. The feeding plate may be secured to the bottom peripheral flange by means of a moveable clasp. Similarly, a feeding platform may be suspended from a suitable location at the top end of the feeder, such as the same hanging means which supports the entire feeder in order to suspend the feeding platform in the bottom of the feeder. The suspended feeding platform is designed to hold water in its center region as well as fruit or other foods. The center feeding plate may be easily removed from the outer ring portion for cleaning or replenishment of food or water. In this orientation, the top of the feeder will be in a semi-opened orientation, as a result of the securement of the hanging means, to allow the entrance and exit of butterflies and the like through the top as well as through the sidewalls of the feeder.

In accordance with other preferred features of the invention, the mesh material of the sidewalls includes multiple reticulated U-shaped members. These U-shaped members may be made of a variety of materials including metal or wicker of a gauge suitable to provide the desired mesh size for the feeder.

In accordance with a special alternate embodiment of the invention, a means for supporting a feeding tray may be incorporated into the bottom portion of the feeder, when the feeder is in its vertical orientation. Two supporting horizontal side segments may be attached by glue, a moveable clasp, or other means to the bottom circumferential rib. These side segments will allow for an opening in the center of the bottom of the feeder providing a like space for the tray to be placed therein. The tray is specially constructed to have a turned up edge around its perimeter to allow the tray to fit snugly down into the side segments, as well as to prevent the food in the tray from sliding out. This arrangement allows the tray to be removed from below the feeder by hand in order to replace the food or for cleaning. The tray may be replaced into the feeder by simply tilting the tray slightly and lifting it upwardly into the opening in the bottom of the feeder between the two side segments. The tray may then be lowered onto the side segments and secured into position by the generally parallel contact of the bottom surface of the lip of the tray with the top surface at the edges of the side segments.

In accordance with still another aspect of the invention, accessories may be provided which make the new and improved collapsible protective enclosure and feeder more alluring to butterflies. Such accessories may include: an ant guard to restrict ants from crawling down onto the feeder having a vertically hanging rod member upon which a water bowl may be slidably placed; a removable rain shield suspended above the feeder; tines or spears for fruit or other relatively soft foods which protrude from the sidewalls or may be combined into a hanging group suspended inside or outside the device; scent baskets containing aromatic oil; hanging baskets for rock candy or other sweets; or other useful accessories.

Other objects and advantages provided by the present invention will become apparent from the following detailed description of the invention, taken in conjunction with the drawings, in which:

BRIEF DESCRIPTION OF THE DRAWINGS

FIG. 1 is a perspective view of the improved collapsible protective enclosure and feeder in accordance with an embodiment of the invention in a vertical orientation;

FIG. 2 is a perspective view of the improved collapsible protective enclosure and feeder in accordance with another embodiment of the invention in a horizontal orientation;

FIG. 3 is an enlarged view of the improved collapsible protective enclosure and feeder in accordance with the invention illustrating the preferred structure of the mesh sidewalls;

FIG. 4 is a perspective, partially cut-away view of the improved collapsible protective enclosure and feeder in accordance with a further embodiment illustrating a bottom feeding tray;

FIG. 5 is a perspective view of the improved suspended feeding platform in accordance with the present invention;

FIG. 6 is a cross-sectional view of the improved feeding platform illustrated in FIG. 5;

FIG. 7 is a side elevation of an ant guard and rain shield; and

FIG. 8 is a perspective view of a component of the ant guard illustrated in FIG. 7.

DETAILED DESCRIPTION OF THE PREFERRED EMBODIMENTS

Referring now to FIGS. 1-2, the new and improved collapsible protective enclosure and feeder, generally referred to by reference numeral 10, is shown. The collapsible protective enclosure and feeder typically has a diameter between about 10 and 40 cm. FIGS. 1-3 illustrate the mesh sidewall structure of the collapsible feeder 10 which includes circumferential ribs 11. The mesh sidewalls include U-shaped members 12 having leg portions 13 and an apex portion 14. The leg portions 13 of the U-shaped members 12 have a spacing between each leg of approximately 4 to 12 cm. The leg portions 13 are pivotally attached to the circumferential rib 11 at attachment points 15. The U-shaped members 12 oppose each other at their apexes 14 and are joined via an attachment means 16. Such a structure allows the feeder to collapse by having the U-shaped members 12 hinge at the attachment points 15 on the circumferential rib 11, outwardly rotating the apex portion 14 and attachment means 16 until the circumferential ribs 11 come into contact with one another, completely collapsing the protective enclosure and feeder.

As shown in FIGS. 1-2, the collapsible feeder 10 includes a peripheral flange 19 which defines the top and bottom portion and the ends of the collapsible feeder 10 in its FIG. 1 and FIG. 2 embodiments, respectively. The peripheral flange 19 is pivotally attached to the circumferential rib 11 at attachment point 20, but is unattached at the apex 21 allowing for the peripheral flange 19 to move outwardly to open the end of the feeder 10, as shown in FIG. 2; or the peripheral flange may be moved inwardly to close the bottom end of the feeder 10, as shown in FIG. 1. In its closed position, peripheral flange 19 may be used to support a feeding plate 23, used to hold fruit 24 or other foods. In its preferred embodiment, the collapsible protective enclosure and feeder 10 may be suspended in either a vertical (FIG. 1) or horizontal (FIG. 2) orientation. As shown in FIG. 1 a support member 25 is attached to apex portions 14 of peripheral flange 19. As shown in FIG. 2 a support member 26 is attached to the sidewall of the feeder 10 at a central circumferential rib 11.

Referring particularly to FIG. 4, in accordance with the alternate embodiment of the present invention illustrated thereby, horizontal side segments 28 are attached to the bottom circumferential rib 29 in order to support a feeding tray 30. The illustrated feeding tray 30 has a lip 31 around the perimeter of the feeding tray 30. Which aids the feeding tray 30 in fitting snugly down into and between the horizontal side segments 28.

With reference to FIGS. 5-6, in accordance with this invention, the improved suspended feeding platform 33 includes a ring 34, having supporting members 35 attached to the ring 34 at attachment points 36. Feeding platform 33 includes a removable tray 37 having an upper rim 38, an intermediate level 39 and a lower platform 40. When placed into the ring 34, the upper rim fits securely in parallel abutment with the top of the ring surface 34 (FIG. 6). Lower platform 40 may be used, for example, as a water source. In accordance with the present invention, the feeding platform may be suspended within the collapsible feeder while it is in a horizontal or vertical orientation via the supporting members 35.

With respect to FIGS. 7-8, in accordance with a preferred embodiment of this invention, an ant guard assembly 44 prevents ants from crawling down onto the feeder. It includes an upper eye ring 45 for suspending the ant guard assembly 44 from an overhang support. The ant guard assembly 44 also includes a lower eye ring 47 for suspending the collapsible protective enclosure and feeder 46. The upper eye ring 45 and lower eye ring 47 are located at opposite ends of a rod 48 which is typically between about 10 and 25 cm long. A retaining or supporting member such as bottom plate 49 can be secured thereto, which retaining member can be rigidly affixed just above the lower eye ring 47. The bottom plate 49 supports a guard component provided to prevent ants or other small crawling life forms which would be attracted by the food within the protective enclosure and feeder from crawling down the suspension means and into the feeder. The guard component can take the form of a liquid-filled container or bowl 51 which provide a liquid barrier which cannot be traversed by the ants or the like. A plate or rain shield 50 can also be included for providing some protection from the weather. Either or both of the rain shield 50 and the guard component 51 may be slidably removed and replaced from the ant guard assembly 44 by sliding up or down the rod 48 over the upper eye ring 45. The guard 51 includes a center tube 52 which slidably fits over the rod 48. Typically, the guard 51 has a diameter between about 5 and 20 cm and a wall height between about 3 and 10 cm. Shield 50 can have a diameter of between about 25 and 45 cm.

Although the present invention has been described with reference to certain preferred embodiments, modifications or changes may be made therein by those skilled in this art. For example, although the preferred collapsible protective enclosure and feeder has been illustrated including three circumferential ribs, the new and improved collapsible protective enclosure and feeder may include only two circumferential ribs, or more than three circumferential ribs. An embodiment having multiple circumferential ribs would enable the cage to be molded into varying decorative shapes beyond the cylindrical shape of the illustrated embodiments. Further, although the preferred embodiment of the collapsible cage and feeder has been illustrated including U-shaped members to form the mesh sidewalls, the new and improved collapsible cage and feeder may include mesh sidewalls having varying members, structures and materials, provided the spacing allows the ready ingress and egress of butterflies and the like while protecting them from other, larger animals, especially birds.

All such obvious modifications may be made herein by those skilled in this art, without departing from the scope and spirit of the present invention as defined by the appended claims.

I claim:

1. A collapsible protective enclosure and feeder for butterflies and the like, comprising:
a generally cylindrical sidewall including at least two circumferential ribs having therebetween a mesh material having members sufficiently spaced from each other by a distance to have said mesh material allow the ingress and egress of butterflies and the like while excluding larger animals, each of said circumferential ribs generally defining an end of the protective enclosure and feeder;
a peripheral flange having an attachment end pivotally mounted to one of said circumferential ribs, said peripheral flange further having a free end generally opposed to said attachment end, said peripheral flange being movable inwardly to close or outwardly to open one of said ends of the protective enclosure and feeder;
a feeding plate suspended within said protective enclosure and feeder;
suspension means for supporting said feeding plate; and,
hanging means for hanging said protective enclosure and feeder from an overhang support.

2. The device of claim 1, wherein said hanging means includes a filament-like member attached to said peripheral flange for hanging said device in a generally vertical orientation.

3. The device of claim 1, wherein said hanging means includes a member attached to said sidewall at a generally central circumferential rib for hanging said device in a generally horizontal orientation.

4. The device of claim 1, wherein said distance by which said sidewall members are spaced from each other is between approximately 4 and approximately 12 cm.

5. The device of claim 1, further including a feeding plate resting on a bottom surface of the device.

6. The device of claim 5, further including means for securing a feeding plate to a bottom portion of the protective enclosure.

7. The device of claim 1, wherein said hanging means includes an ant guard assembly positioned generally along said hanging means, and said ant guard assembly includes a body of liquid whereby ants and the like which crawl down said hanging means are restricted by the body of liquid from entering the protective enclosure and feeder.

8. The device of claim 7, wherein said ant guard assembly includes a rod having an upper eye ring to hang said rod in a vertical orientation, said rod having at its bottom end a secured plate for supporting a container for the body of liquid, said container having a center tube allowing said container to be slidably removable from said rod, said ant guard assembly also including a lower eye ring for hanging said protective enclosure and feeder.

9. The device of claim 7, wherein said ant guard assembly further includes a plate having sufficient diameter to shield said protective enclosure and feeder from rain and the like, said plate also having a hole in the center to be slidably removable from said rod.

10. A collapsible protective enclosure for feeding butterflies and the like comprising:
a generally cylindrical sidewall having generally opposing peripheral ends, said sidewalls including a circumferential rib located at each of said peripheral ends of the sidewall;
said sidewall being made of multiple U-shaped members assembled to form a mesh material having a spacing between said U-shaped members sufficient to have said mesh material allow ingress and egress of butterflies and the like while excluding larger animals, said U-shaped members each having an apex portion and leg portions;

said leg portions of at least some of the U-shaped members are pivotally mounted to each of said circumferential ribs, pairs of said U-shaped members generally oppose each other at their respective apex portions wherein said apex portions are joined via attachment means between said U-shaped members, said attachment means are spaced generally concentrically at a generally uniform distance from said circumferential ribs, each said pair of U-shaped members defining a sidewall segment, each said sidewall segment being rotatable on said ribs to impart a collapsibility characteristic to said protective enclosure;

a peripheral flange pivotally secured to one of said peripheral ends of the sidewall, said peripheral flange being defined by multiple ones of said U-shaped members pivotally attached at their said leg portions to said circumferential rib and unattached at their said apex portions, said peripheral flange being movable inwardly to close the end of said protective enclosure and outwardly to open said end of the protective enclosure;

said protective enclosure further including a feeding platform including a circular rim having a multi-level plate insertible into said rim whereby the uppermost level of said plate is in substantially parallel contact with said rim, said feeding platform including means for supporting same within said protective enclosure; and means for hanging said protective enclosure from an overhang support.

11. The device of claim 10, wherein said spacing between said U-shaped members is between approximately 4 and approximately 12 cm.

12. The device of claim 10, wherein a first said U-shaped member is adjacent a second said U-shaped member on one side and adjacent a third said U-shaped member on an opposite side, a first leg portion of said first U-shaped member crosses in front of a first leg portion of said second U-shaped member, a second leg portion of said first U-shaped member crosses behind a first leg portion of said third U-shaped member, said first leg portion of said first U-shaped member being pivotally attached to said circumferential rib at a location between said first leg portion and said second leg portion of said second U-shaped member, said second leg portion of said first U-shaped member pivotally attached to said circumferential rib at a location between said first leg portion and said second leg portion of said third U-shaped member, said first leg portion of said second U-shaped member and said first leg portion of said third U-shaped member being pivotally attached to said circumferential rib at a location between said first leg portion and said second leg portion of said first U-shaped member, said first leg portion of said second U-shaped member and said first leg portion of said third U-shaped member having located therebetween legs of opposed fourth an fifth U-shaped members which are pivotally attached to said circumferential rib.

13. The device of claim 10, wherein said feeding platform includes at least three attachment points on said rib and suspension members secured to the attachment points to suspend said feeding platform within said protective enclosure.

14. The device of claim 13, wherein a feeding plate rests on a bottom peripheral flange which is in its closed position.

15. The device of claim 14, wherein said feeding plate is secured to the bottom peripheral flange by a moveable clasp.

16. The device of claim 10, wherein said protective enclosure is collapsible into a generally flat orientation for ease of transport and storage.

17. The device of claim 10, wherein said generally cylindrical sidewall has a diameter of between approximately 10 and approximately 40 cm.

18. A collapsible protective enclosure for feeding butterflies and the like, comprising:

a generally cylindrical sidewall having generally opposing peripheral ends, said sidewall including at least two circumferential ribs located at each of said peripheral ends of the sidewall, said sidewall being of a mesh structure having multiple reticulated U-shaped members of sufficient diameter to have said mesh structure allow ingress and egress of butterflies and the like while excluding larger animals, said U-shaped members having an apex portion and leg portions;

said leg portions of at least some of the U-shaped members are pivotally mounted to said circumferential ribs, pairs of said U-shaped members generally oppose each other at their respective apex portions wherein said apex portions are joined via attachment means between said U-shaped members, said attachment means are spaced generally concentrically at a generally uniform distance from said circumferential ribs, each said pair of U-shaped members defining a sidewall segment, each said sidewall segment being rotatable on one of said ribs to impart a collapsibility characteristic to said protective enclosure;

said sidewall having at a top one of said peripheral ends a peripheral flange defined by multiple ones of said U-shaped members pivotally attached at their said leg portions to said circumferential rib and unattached at their said apex portions, said peripheral flange being movable inwardly to close said top or outwardly to open said top of said protective enclosure; and a feeding tray at a bottom one of said peripheral ends of the sidewall.

19. The device of claim 18, wherein said feeding tray includes a rectangular tray member having a generally upstanding peripheral lip, said feeding tray being securely placed in the bottom of said cage between two side segments attached to a bottom circumferential rib.

20. The device of claim 18, further including means for hanging the protective enclosure from an overhanging support, said hanging means including a member attached to the peripheral flange for hanging said device in a generally vertical orientation.

21. The device of claim 18, wherein said sidewall provides spacing between the U-shaped members, said spacing being between about 4 and about 12 cm.

22. The device of claim 18, wherein said protective enclosure is collapsible into a generally flat orientation.

* * * * *